(12) United States Patent
Moore

(10) Patent No.: US 9,707,277 B2
(45) Date of Patent: *Jul. 18, 2017

(54) PRESERVATION OF THE BIOLOGICAL ACTIVITY OF UNDENATURED TYPE II COLLAGEN

(71) Applicant: Eugene R. Moore, Midland, MI (US)

(72) Inventor: Eugene R. Moore, Midland, MI (US)

(73) Assignee: CARTILAST II LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/545,910

(22) Filed: Jul. 6, 2015

(65) Prior Publication Data

US 2015/0313966 A1    Nov. 5, 2015

Related U.S. Application Data

(60) Continuation-in-part of application No. 13/986,572, filed on May 15, 2013, now Pat. No. 9,101,608, and a division of application No. 13/694,971, filed on Jan. 23, 2013, now Pat. No. 9,023,416.

(51) Int. Cl.
  *A61K 38/39* (2006.01)
  *A61K 35/57* (2015.01)
  *A61K 38/01* (2006.01)

(52) U.S. Cl.
  CPC ............. *A61K 38/39* (2013.01); *A61K 35/57* (2013.01); *A61K 38/014* (2013.01)

(58) Field of Classification Search
  USPC ...................................... 424/93.7
  See application file for complete search history.

*Primary Examiner* — Sharmila G. Landau
*Assistant Examiner* — Stephanie McNeil
(74) *Attorney, Agent, or Firm* — Timothy S. Stevens

(57) ABSTRACT

The instant invention is the storage of Type II collagen containing tissue in carbonated water. Such Type II collagen is useful for alleviating the symptoms of arthritis in mammals as well as the treatment of arthritis in mammals. Such Type II collagen is also useful for the prevention of arthritis in mammals. The instant invention is also a method for the preparation of a nutritional supplement that includes the steps of: (a) separating water-insoluble undenatured Type II collagen containing animal tissue from animal tissue not containing Type II collagen; (b) subdividing and sterilizing said tissue under conditions which do not change the original structure of the Type II collagen to produce a subdivided and sterilized product; (c) packaging the subdivided and sterilized product in carbonated water.

8 Claims, 1 Drawing Sheet

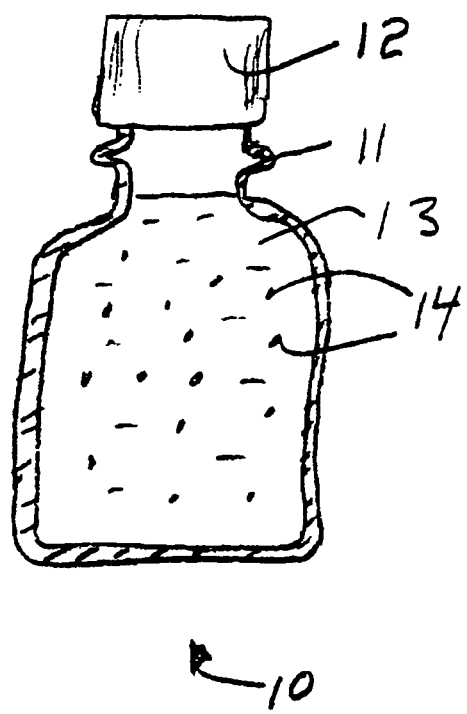

PRESERVATION OF THE BIOLOGICAL ACTIVITY OF UNDENATURED TYPE II COLLAGEN

This application is a continuation-in-part of US patent claims priority to U.S. patent application Ser. No. 13/986,572 filed May 15, 2013. Among other things, this invention provides a technique for storing and shipping therapeutic amounts of animal tissue containing a therapeutic amount of undenatured Type II collagen and an improved method of preparing and maintaining such collagen in a pure, useful, and undenatured state so it can be consumed and utilized for ameliorating the effects of auto-immune arthritis in warm blooded mammals including equine such as horses, donkeys and mules or canine such as dogs and wolfs, and humans.

BACKGROUND OF THE INVENTION

Arthritis is a painful and often crippling disease that initially results in painful, swollen, and inflamed joints. It often progresses to deform or completely destroy joints that then require replacement. This disease is a result of the body mistakenly attacking type II collagen, which is the major structural component of cartilage tissue. One function of cartilage tissue is that it serves as a lubricant in the joints, keeping bone from rubbing on bone. As the disease progresses and more of the cartilage is destroyed, bone does begin to wear on bone. The two most prominent types of arthritis are rheumatoid arthritis and osteoarthritis. The usefulness of undenatured Type II Collagen has been shown in ameliorating the symptoms of Osteoarthritis in humans (International Journal of Medical Sciences, 2009; 6(6); 312-321), Horses (Journal of Veterinary Pharmacology and Therapeutics 32, 577-584, 2009), and Dogs (Journal of Veterinary Pharmacology and Therapeutics 28, 385-390, 2005), which are all here fully incorporated by reference.

In order to initiate rheumatoid arthritis, it appears that an individual must have an inherent susceptibility. There is now evidence that, in susceptible people, this disease is initiated by exposure to the relatively common Epstein-Barr virus. The ability of the Epstein-Barr virus to initiate Rheumatoid Arthritis has been linked to a key amino acid sequence which is identical to a sequence found in human Type II collagen. Thus, in generating antibodies to destroy the Epstein-Barr virus the body generates antibodies that are also capable of attacking its own collagen.

Osteoarthritis has recently been found to also be an attack by the autoimmune system on cartilage. It is interesting that osteoarthritis occurs in animal species that do not, as a species, have rheumatoid arthritis. These species include canine such as dogs and equine such as horses. Osteoarthritis is strongly related to age in both animals and humans. One likely reason for this age related effect is an alternate method for the autoimmune system to be activated to initiate an attack on the body's cartilage. Such activation method may involve the very life sustaining act of metabolism. In order to convert carbon based food into $CO_2$ and energy, the body creates massive numbers (many millions) of reactive oxygen species (ROS). In this process of breaking down food and producing energy, DNA chain breakage or other damage, in the average person, is said to occur over a million times per day. A large portion of this damage relates to cleavage of the DNA, which is quickly repaired or destroyed by the immune system. This very routine action of the body's immune system is absolutely vital to human life. Some of the damaged molecules have the potential to cause the immune system to generate antibodies that are then capable of attacking the body's own collagen. When a body ages, a combination of effects cause it to become more susceptible to this osteoarthritis inducement. In some cases the DNA damage repair system becomes weaker. In other cases there may simply be a gradual built up and accumulation of the water soluble molecular fragments that have the potential to generate antibodies that are capable of attacking the body's own collagen. When a sufficient accumulation of these water soluble molecular fragments occurs, the collagen destroying antibodies are activated.

In order to study the effect of proposed techniques for amelioration of arthritis, it is necessary to have arthritic animals. Two techniques to artificially induce arthritis in rats have been developed. These inducements have been accomplished, more quickly than for osteoarthritis in humans, but in a similar manner. With rats the newer technique is by the intradermal (under the skin) injection of a broken down, water soluble fragment of undenatured Type II collagen (extracted from chicken cartilage). This technique has been termed Collagen Induced Arthritis (CIA). The second and older technique is accomplished by intradermal injection of the well known *Microbacterium tuberculosis* (MT).

It was also shown that rats could be prevented from getting arthritis induced or the effects of inducement greatly reduced. This prevention was accomplished by feeding (or arterial injection) of the same broken down, water soluble fragment of Type II collagen for several days prior to the attempted inducement. It was also shown that, once arthritis has been induced, the effects of the disease could be reduced by the continual oral administration of the same broken down, water soluble fragment of Type II collagen. In later clinical studies with humans having arthritis oral administration of the broken down, water soluble fragment of Type II collagen was similarly beneficial in reducing the effects of the disease.

Oral administration of this broken down, water soluble, undenatured fragment of Type II collagen represents the very first technique for amelioration of the symptoms of arthritis that represented a reversal rather than simply a slowing of the progress of the disease. This oral technique is believed to effectively reverse the debilitating effects of arthritis by causing desensitization to Type II collagen. After this desensitization the body stops producing antibodies that destroy its own collagen. This process has been called "oral tolerization" which is a partially understood process which the body uses to stop a person's immune system from treating food as a hostile foreign body. If foreign proteins are introduced via the digestive system, the body automatically suppresses the immune system responses to these proteins. It is a technique that has been used in the past to ameliorate simple allergies such as an allergic reaction to poison ivy or pollen.

While this oral administration of a broken down, undenatured, water soluble fragments of Type II collagen represents a long sought and highly desired technique for amelioration of the symptoms of arthritis, the broken down, water soluble fragments of Type II collagen are difficult to prepare. Typically they are extracted from the tiny sterile cartilages of 2.5 week old chicks. In a preparation of this prior art, eighty animals were required to produce 19 g of cleaned sterile cartilage dissected free of surrounding tissue. It is typical of the prior art to perform up to seven operations, consisting of extractions or digestions, on each batch of tissue in order to obtain the broken down, water soluble fragment of Type II collagen. The procedure of this prior art is thus seen to have several serious deficiencies. An extremely large number of animals are required to obtain a small amount of the desired product. The purification procedure is very time consuming, requiring multiple extractions, digestions, and precipitations. Sometimes ultra filtration of the final product is required as a final step to remove pathogens from the water soluble product.

It was later discovered by Moore that it was not necessary to break the undenatured Type II collagen into a water soluble state to obtain the full anti arthritic effect when ingested. Moore in U.S. Pat. Nos. 5,645,581; 5,637,321; 5,529,786; and 5,750,144 (which are hereby fully incorporated by reference) surprisingly found that the normal digestive process was sufficient. That is, when the whole, undenatured cartilage is digested, the effective amino acid sequence is separated and passed into the blood stream where it can reduce the symptoms of arthritis. This accomplishes the same goal as the earlier experiments with rats where the desired effect was obtained by direct injections of the water soluble fragment into the blood stream. This 26 amino acid sequence has been identified and presented by Trentham in U.S. Pat. No. 5,399,347 (which patent is hereby incorporated in full by reference). It was shown that this sequence, though difficult to prepare from sequencing monomeric amino acids, had amelioration effects for arthritis.

In the above-referenced Moore patents it was found preferable to utilize the much larger cartilage from young four to six or more month old chickens. Such usage made more cartilage available and was also easier to maintain in a sanitary state. Although Moore preferred chicken cartilage, Moore taught that cartilage from other animal tissue containing Type II collagen could be effectively utilized. Bovine or porcine cartilage, or vitreous humor of eyes, for example, could be used if desired, although the solid cartilage was preferred and chicken sternal cartilage was most preferred. Moore's technique for preparation of cartilage for oral administration to humans consisted of first dissected the cartilage free of surrounding tissues so that the cartilage could be, for example, diced into smaller pieces. The diced cartilage was then sterilized by means known in the art and, for example, formed into capsules containing therapeutic levels of Type II collagen, said levels being at least about 0.01 gram and preferably from about 0.1 to about 0.5 grams of cartilage to provide a therapeutic dose. The use of more mature chickens in the Moore approach was surprising in view of the prior art which taught only the use of chicks of less than three weeks of age. The usefulness of the more mature chickens allowed an almost 100 fold increase in the amount of harvestable cartilage from a single animal. This, of course, made the desired product more readily available in therapeutic quantities, and also greatly decreased the possibility of micro-contamination due to the reduced handling during separation from relatively fewer animals.

It is difficult to preserve cartilage in its native undenatured state and thus maintain its effectiveness in alleviating the symptoms of autoimmune diseases. In the past, it has been possible to preserve the cartilage by two techniques. First, by cleansing, cooling, and storing the cartilage at very low temperatures Moore in the above patents, demonstrated that the collagen can be preserved successfully for an extended period. This storage is without the growth of harmful pathogens or change in structure of the collagen which would cause it to become denatured and thus lose its effectiveness. This process has the requirement to cleanse prior to cooling, by sterilization, for example, with chlorine producing agents and/or hydrogen peroxide. Second, by drying cleansed cartilage under special low temperature conditions, in the presence of an inorganic salt, the storage life of the collagen is greatly extended. This was shown in the work of Schilling et. al. (U.S. Pat. No. 7,083,820), which is hereby fully incorporated herein by reference. The Schilling procedure has the disadvantage of requiring a long, low temperature drying step.

In cleaning and preparation for use, the cartilage is difficult to completely free from biological contamination such as pathogens and other microbes in order to maintain its safety. These pathogens, other microbes, and the like must be removed to render the undenatured Type II collagen fit for human or animal consumption, even after extensive storage. It is desired to have the cartilage free of additives and easy to handle, store, ship, and consume.

The use of carbon dioxide gas to inhibit the growth of micro organisms and extend the storage life of fruits, vegetables and meats is well known. This knowledge goes back to the time of the Romans who would pack caves with fruit to let the off gasses due to ripening, largely $CO_2$, accumulate and slow the ripening and thus prolong the eatable quality of the food. This extension in usefulness of the produce is sometimes measured in hours in the case of cut fruit for example. Such extension in useful life is often measured in days for items such as meat and poultry. The inhibition in ripening for uncut apples and other thickly skinned whole fruits is often measured in weeks as is pointed out, for example, in the Journal of food protection (Daniels; volume 48, issue 6, 1985, pages 537-537) which is hereby fully incorporated by reference.

The use of carbon dioxide has long been recognized as a means to merely retard the deterioration and spoilage of butchered meat or otherwise comminuted food types of substances and thus increase, in a small way, the useful storage life. This retardation has involved addition of at best only a few additional days of useful life. A summary is shown in the above article by Daniels. Brecht, (Food Technology Vol 34, 1980; page 45-50) in another summary of the use of controlled atmosphere to retard spoilage of produce cites some negative results on the use of $CO_2$. Acetaldehyde accumulation for one example or ultrastructure alterations for another example that suggested that $CO_2$ induces an uncontrolled breakdown of tissue. The product of our invention does not have these negative results.

Ogilvy (Food technology; Vol. 5; 1951; pp 97-102; "Postmortem Changes in Meats II. The Effects of Atmospheres Containing Carbon Dioxide in Prolonging the Storage Life of Cut-up Chicken" examined the effects of $CO_2$ on prolonging the storage life of cut-up chicken. He used the concentration of slime forming bacteria reaching a count or $2 \times 10^8$ per square centimeter as an end of useful life. This level is believed to be well above the slime forming bacteria concentration when a visible haze forms in the slightly contaminated cartilage stored in the aqueous $CO_2$ of our invention. Ogilvy also noted a common problem when $CO_2$ is used to store meat or fish. That problem is discoloration, with a undesired dark brown color developing in bird flesh. The products of our invention are surprisingly void of such discoloration at even the highest $CO_2$ levels. The product of our invention is very white, or clear unless purposefully colored with an added die or other coloring material. Ansuetto et al ("Microatmospheric packaging of Apples"; Paper presented at Institute of Food Technologists Annual Meeting, Anaheim Calif.; Jun. 10-13, 1984) examined straw berries, along with other produce. He cited data showing that strawberries are particularly susceptible to decay. He extended storage from less than 3 days to about 6 days using a 30% $CO_2$ atmosphere in the packages. He also pointed out some cases where higher levels of $CO_2$ are harmful, where berries must be shipped with "scrubbers" such as lime.

SUMMARY OF THE INVENTION

The instant invention solves the above-mentioned problems and the discovery of new applications for the use of carbon dioxide provided the carbon dioxide is dissolved in an "aqueous medium" (defined herein as a liquid medium comprising water, preferably more than fifty percent water by weight, more preferably more than seventy five percent water by weight and yet more preferably more than ninety percent water by weight). The instant invention completely eliminates the requirement to add up to 40-60% or more of a salt to the cartilage. In the preferred practice of the instant invention, the need for the long, low temperature drying step is eliminated. The instant invention further provides a safe method of storing the cartilage (or other tissue). The product of our invention can be packaged so that a consumer can easily vary a dose size to find a preferred dose, and repeat that dose.

The liquid product packaging of the instant invention offers advantages over the dry product of the '820 patent. These advantages come from the potential to be manufactured, wholesaled, distributed, and consumed by those that have experience with or a preference for a liquid product. A particular advantage is liquid products ability to be promoted by existing distributors that promote liquid packaged products. Liquid product can also be placed into retail locations that are relatively convenient and selectively attractive to thirsty potential consumers. Any company that manufactures, wholesales, distributes, or retails any drink, sports drink, health promoting drink, or joint-health promoting drink might take advantage of their experience with liquid product or the experience of those in their existing supply chain. Liquid packaged product offers the advantage of being co-located with bottled soda and/or liquid health promoting drinks. For example, liquid product appears behind glass doors or refrigerators near cash registers located in grocer stores or health clubs Distinct and convenient point of sale retail locations which allow a consumer to read labels while waiting in line, become informed of the product, and see product which might otherwise only be seen elsewhere at the retail location in more obscure places. We have surprisingly found that when properly prepared cartilage is stored in carbonated water, that the storage life is measured in years and appears to be unlimited. Prior art of $CO_2$ storage to preserve food value gives no indication of maintaining effectiveness in ameliorating the effect of arthritis.

More specifically, in one embodiment the instant invention is a method for storing Type II collagen containing tissue in an aqueous medium, comprising the step of surrounding the tissue with the aqueous medium, the aqueous medium containing more than 0.01 percent carbon dioxide by weight. In another embodiment, the instant invention is a method for alleviating the symptoms of arthritis in mammals which comprises orally administering a composition obtained by separating water-insoluble undenatured Type II collagen containing animal tissue from animal tissue not containing Type II collagen, subdividing and sterilizing said tissue under conditions which do not change the original structure of the Type II collagen to produce a subdivided and sterilized product, storing the subdivided and sterilized product in an aqueous medium containing more than 0.01 percent carbon dioxide by weight to produce the composition, which composition is administered in an amount effective and for a time effective to alleviate such symptoms.

In yet another embodiment, the instant invention is a process for the treatment of arthritis in mammals which consists of the steps of: (a) removing, under sterile conditions, tissue containing mostly Type II collagen to produce a sterile tissue; (b) storing the sterile tissue in an aqueous medium containing more than 0.01 percent carbon dioxide by weight to produce a stored sterile tissue; and (c) orally ingesting therapeutic quantities of said stored sterile tissue. In still yet another embodiment, the instant invention is a method for the prevention of arthritis in mammals comprising the steps of: (a) removing, under sterile conditions tissue containing Type II collagen to produce a sterile tissue; (b) storing the sterile tissue in an aqueous medium containing more than 0.0.01 percent carbon dioxide by weight to produce a stored sterile tissue; and (c) orally ingesting a quantity of said stored sterile tissue sufficient to prevent arthritis in the mammal. In another embodiment, the instant invention is a method for the preparation of a nutritional supplement, comprising the steps of: (a) separating water-insoluble undenatured Type II collagen containing animal tissue from most animal tissue not containing Type II collagen; (b) subdividing and sterilizing said tissue under conditions which do not change the original structure of the Type II collagen to produce a subdivided and sterilized product; (c) packaging the subdivided and sterilized product in an aqueous medium containing more than 0.01 percent carbon dioxide by weight. In a yet further embodiment, the instant invention is a method for freezing animal tissue containing undenatured Type II collagen by the step of cooling the tissue at a rate sufficiently slow so that the Type II collagen essentially remains in the undenatured state.

BRIEF DESCRIPTION OF THE DRAWINGS

FIG. 1 is a side view, part in full and part in cross-section, of a suspension of Type II collagen containing cartilage particles suspended in carbonated water.

DETAILED DESCRIPTION OF THE INVENTION

The process of this invention comprises the use of aqueous carbon dioxide ($CO_2$) for the safe storage of type II collagen while maintaining the biological activity of this cartilage tissue (or other tissue containing type II collagen). The process effectively eliminates the growth of trace pathogens as well as microbes that might cause spoilage. More specifically the process of the present invention involves storing said cartilage for relatively long periods of time in the presence of aqueous $CO_2$, preferably after treating with antimicrobial agents.

The minimum concentration of the carbon dioxide in the aqueous medium of the instant invention is about 100 parts per million (PPM) by weight. More preferably, the concentration of carbon dioxide used in the instant invention is 1,000 parts per million or more by weight. Most preferably, the concentration of carbon dioxide used in the instant invention is 3,000 parts per million or more by weight. As storage pressure is increased the $CO_2$ content of the aqueous medium is increased. The upper limit of $CO_2$ appears to only be limited by the pressure limit of the desired storage vessel or pressure at which, upon opening the vessel, the product of the instant invention is expelled in an unacceptable manner. When water is used in the instant invention it is preferable that the water be supersaturated with carbon dioxide and stored in a sealed pressure resistant container. Said storage conditions, in addition to eliminating any remaining traces of pathogens and microbes that might cause spoilage, have been shown to surprisingly keep the cartilage in its unaltered, undenatured, and thus most effective state.

As disclosed in the four previously mentioned patents of Dr. Eugene Moore, the use of undenatured Type II collagen reduces the symptoms of rheumatoid arthritis. As mentioned above, a recent clinical trial (International Journal of Medical Sciences, 2009; 6(6):312-321) has also shown effectiveness of undenatured cartilage against Osteoarthritis. Osteoarthritis combined with Rheumatoid Arthritis present a very serious health problem, affecting a large portion of the worlds aging population In a preferred practice of this invention, after first removing most or all visible physical contaminants, an antimicrobial agent is used to remove most pathogens or microbes that might cause spoilage. An antimicrobial agent such as sulfur dioxide, ethylene oxide, chlorine, sodium hypochlorite (NaOCl), or a source of active oxygen such as hydrogen peroxide ($H_2O_2$) are useful to carry out this sterilization function. Carefully controlled x-rays or the like may in some cases be useful and desired. This treatment might involve x-rays, gamma rays, electron beams or ultra violet light. Preferably the sterilization agent is chlorine, sodium hypochlorite or a source of active oxygen such as hydrogen peroxide. It is important to control the dose so that most pathogens are destroyed without significant denaturing of the collagen. This sterilization function may be carried out initially as well as during processing. The idea is to have most or preferably all of these pathogens and antimicrobial agents removed or destroyed before storage in a $CO_2$ containing media, thereby lengthening the safe storage period. When carbonated water is used, a visual observation of the stored product is one indicator of undesirable growth of pathogens or other microbial agents. In this case haze or cloudiness is one indicator of growth while another indicator is discoloration. Therapeutic levels of Type II collagen in the instant invention are at least about 0.01 gram and preferably from about 0.1 to about 0.5 grams.

It is desired that the pathogens and microbes be greatly reduced by the above sterilization type pretreatment. If such pretreatment is not carried out, storage time of the cartilage is significantly shortened. Successful or useful storage time, however, for this untreated cartilage is lengthened by increasing the $CO_2$ concentration in the liquid.

While special pressure vessels could easily be obtained to package and ship cartilage in bulk, where desired, we generally prefer to package and ship in readily available containers and bottles that are already designed for the moderate pressures required for commercial carbonated beverages, such as soft drinks, vitamin or mineral drinks, and the like. Plastic bottles such as those produced from polyethylene terephthalate (PET) are preferred for medium term storage, or for longer term storage when thin non permeable coatings are applied internally. Surprisingly, single or multiple dose packaging in thinner plastic bubble like containers using low permeability plastics such as vinyl chloride/vinylidene chloride copolymers are operable. Multiple dose packaging in larger self metering plastic bottles is in some cases desirable. Glass bottles are preferred for longest term storage. The lower permeability of glass allows for almost prefect retention of the $CO_2$. However, glass lined plastic bottles (such as plastic bottles the interior of which are coated with a thin glass like layer by a plasma vapor deposition process) are also preferred in the instant invention because such containers are shatter resistant and have greatly reduced permeability. Referring now to FIG. 1, therein is shown a preferred embodiment 10 of the instant invention wherein a glass bottle 11 having screw cap 12 contains a suspension of Type II collagen containing cartilage particles 14 in carbonated water 13.

After the cartilage is free of most or all of the surrounding flesh and preferable treated with one or more antimicrobial agents it can be placed into the aqueous $CO_2$ environment. If the cartilage is from the chicken sternum, the pieces are small enough to even be stored whole in small readily available containers. If the cartilage is from larger animals such as cows or pigs, special containers may be required to store the cartilage in its original physical shape. Cartilage from chicken sternum cartilage is most readily available and is generally preferred, for this and other reasons. Usually chicken sternum cartilage, as received from chicken processing facilities, will contain 10 wt % or more of attached flesh. It is desired, in most cases, to remove this attached flesh, however we have noted that the use of $H_2O_2$ in a final treatment process removes all discoloration and yields a, very pleasing to the eye, all white suspension. Removal of this flesh by hand is labor intensive. We have discovered that mechanical abrasion with material such as common grains or wood pellets for brief periods can remove most of the attached flesh. While there are many approaches to apply this abrasion, we have found that a rotating tumbler works well. When whole cartilage is used it can easily be separated from the smaller abrasive material by common mechanical techniques such as screening. It is preferred to have the abrasive material be combustible. In this combustible case, after separation the abrasive material containing the removed flesh may be dried, if necessary, and used for fuel. In addition to capturing fuel value, a waste disposal problem is avoided In most cases it will be desired to reduce the size of the original cartilage particles by any one of the many techniques well known to those familiar with the art of size reduction. This technique could involve "slicing" equipment that would use sharp blades. This slicing may be carried out by hand with razor blades, or stamping equipment using a matrix of blades. Preferable a rotating blade such as found in a common food blender in an aqueous medium in a $CO_2$ atmosphere. An antifoam agent such as silicon resins, or others familiar to those in the antifoam art, may be used to reduce foam breaking time. In some cases it will be useful to have a large particle, or a collection of particles, equivalent to the desired therapeutic dose individually packaged. This may be accomplished by hand or by automatic weighing equipment. Surface water may be removed by a variety of techniques, such as centrifuging or blotting, before weighing. To get much finer particles, the "blended" chopped particles could be passed through an elongated orifice under very high pressure. The high shear field developed would cause further size reduction. Pressures across a single orifice could be as high as 5-10,000 psig. A series of progressive smaller orifices would allow for progressively smaller particle sizes. In some cases it will be desired to reduce particles to the point that they provide a stable suspension or emulsion. Such emulsions may become semi-transparent of "translucent". We have found that the collagen found in the vitreous humor of bovine eyes, for example, are particularly useful when comminuted in this manner. They produce smaller particles and do so in lower shear fields. This may be due to the type II collagen being so uniformly dispersed and low in concentration. The limit on such size reduction will be limited, in the extreme, by loss of effectiveness as the key 26 amino acid sequence begins to be broken in a significant amount. Suspending agents or emulsification stabilizers may be employed. If particle size is sufficiently reduced the liquid product would become, translucent or transparent which would be desirable for visual appeal in the marketplace. When cartilage is frozen other reduction techniques are useful. These techniques could involve impacting equipment such as hammer mills or the like that would use impact to break up the particles The size reduction technique could also involve the use of particles of cartilage impacting other cartilage particles at high speed and reduced temperature so as to cause breakage in a process that has been called "micronizing". Any of these size reduction processes may be carried out at a variety of reduced temperatures. Often it will be convenient to use liquid nitrogen or dry ice to achieve these temperatures. The "dry ice" ($CO_2$) will be preferred because it aids in the practice of this invention by, in addition to maintaining low temperature, providing a desired $CO_2$ atmosphere during size reduction. In any case it is necessary to control the temperature during grinding, since grinding processes generates heat. Since the collagen structure is changed, that is the collagen is denatured, at elevated temperatures it is necessary to control temperatures during the size reducing comminuting. The exact relationship between temperature and time at that temperature is not known, but suitable conditions will be easily determined by those familiar with the art of size reduction and the denaturization for collagen. Many of the grinding processes, such as those used by Schilling (U.S. Pat. No. 7,083,820) must have instantaneous and localized high temperatures caused by the impacts during grinding. Apparently this heat is applied for too short a time to have a great effect on denaturization of the type II collagen or the effect is too localized (small) to greatly reduce the amount of undenatured collagen. When dealing with bulk average temperatures the following preferences apply in the instant invention. Temperatures approaching 210 F cannot be tolerated except perhaps for only an extremely short time without denaturing the collagen and thus rendering it ineffective for amelioration of the symptoms of arthritis. Temperatures as high as 160 F, can be tolerated for slightly longer times. It is most preferred, however, to have bulk temperatures that do not exceed about 110 F. When temperatures are at this level or lower the cartilage will retain its undenatured structure for at least hours, which is more than enough time for any anticipated, drying, size reduction, or other processing.

Drying at temperatures of 110 F or below will in some cases be desirable in the practice of our invention since some of the useful grinding techniques will be most successful on the more brittle, dried cartilage. Small amounts of anti-clumping agents such as lecithin or hydroxypropyl methylcellulose may be used during this drying stage. The process of drying before fine grinding provides an alternate to using very low temperature grinding to get the finest sizes that can be obtained by mechanical means.

It will often be desirable to have the particles sorted. This sorting might be done during the size reduction stage where particles exit the grinding chamber only when they can pass through a desired screen size. Sorting could also be accomplished by many other techniques familiar to those knowledgeable in the classification art. Techniques such as screening, cyclones, settling, or in an upward flowing gas stream (preferably $CO_2$). This latter technique is often called elution. Alternately the particles could be separated by weight which will be more highly automated as new techniques are developed. Preferably these sorting operations would be carried out in a nitrogen and most preferably a $CO_2$ atmosphere. In some cases a mixture of the two gases would be preferred.

The larger particles might be selected to be the proper dose size for humans, equines, or canines so that one particle per day would be taken for each subject. These particles would then be stored in carbonated water until consumed. Further size reduction could then be obtained by the natural process of chewing.

Finer particles could be blended to produce a slurry, or suspension with carbonated drinks. These drinks would be consumed completely if they contain a single dose. They could alternately be packaged as a concentrate containing a week or a month or more supply. In the case of the concentrate, after mild agitation to promote uniformity, a single dose could be metered out, for example, in a spoon or measuring cup. Special metering containers could also be used. For example, a metering chamber may be provided in a flexible bottle. Squeezing the bottle fills the metering chamber. The contents of the chamber would then be expelled as a therapeutic dose. The container could then be recapped. Such containers are well know in the art of metering gasoline additives, for example. Refrigeration at this point, while not always necessary, would help retain the $CO_2$ in the container for the relatively short storage period and is preferred.

EXAMPLES

Examples 1a and 1b, among other things, demonstrate the effectiveness of carbonated water to store cartilage in an essentially unaltered, undenatured, and sanitary state to not only ameliorate the symptoms of arthritis, but to do it more effectively than other techniques that may be known in the art.

Example 1a

Chicken breasts are purchased from a local supermarket. The sternum cartilage is removed and stripped free of almost all visible flesh. The cartilage is refrigerated for three days then cut into small pieces. One gram is placed into each of four cleaned ordinary plastic carbonated beverage bottles. The cartilage receives no particular surface treatment, such as chlorine or hydrogen peroxide, to destroy microorganisms. In order to test the ability of carbon dioxide to prevent spoilage, $CO_2$ in water is used at three levels. Standard Schweppes™ brand club soda is used, and is chilled before being opened. Boiled and then chilled tap water is used as the diluent. In Table 1, the High level is undiluted club soda water, the Medium is 50% club soda water, the Low is 25% club soda water, and the Zero is pure boiled tap water.

Visual observations of the bottle contents are shown in Table 1. These observations clearly demonstrate the short term preservative advantage of water containing $CO_2$ and the ability, to retard the growth of microorganisms that still remained on the un-pretreated surface of the cartilage.

TABLE 1

Effect of $CO_2$ level on untreated cartilage storage stability

| Time | $CO_2$ concentration | | | |
|------|------|------|------|------|
|  | High | Medium | Low | Zero |
| Start | clear | clear | clear | clear |
| 13 hr | clear | clear | clear | very slight haze |
| 62.5 hr | clear | very slight Haze (1) | slight haze | cloudy |
| 132.5 hr | very slight haze | distinct haze | cloudy | cloudy with sides sucked in |

(1) Note that formation of a haze is a well known indication of undesirable microorganism growth

Example 1b

This example, among other things, demonstrates that increased $CO_2$ content in the water increases storage time. Example 1a is repeated except pressurized $CO_2$ gas is added to the initial chilled club soda water causing the amount of dissolved $CO_2$ to increase by a factor of about 1.5. A significant increase in storage time without haze or other visible change being seen. It is anticipated that a higher level of $CO_2$ would be found that would perform the dual function of: a) destroying pathogens and microorganisms; and b) preserving the effectiveness of the undenatured type II collagen in ameliorating the effects of arthritis.

Example 2

This example, among other things, demonstrates a preferred technique for removing surface contamination before storage. Chicken breasts are purchased from a local supermarket. The sternum cartilage is removed and stripped free of visible flesh. The cartilage is refrigerated then cut into small pieces as in Example 1. In this case the cartilage is treated with a common chlorine releasing compound (NaOCl) before being cut up. The cartilage is drained then exposed to 3 wt % $H_2O_2$ in water as described in Example 1 of U.S. Pat. No. 5,750,144. Two glass bottles of club soda are purchased. One half gram is then placed into a bottle of the, now chilled, club soda and it is tightly resealed. Another half gram is similarly placed into the second bottle that is now filled with previously boiled, to kill any micro organisms, then chilled, water. These samples are then stored at ambient temperatures for an extended period of time and observed periodically. It is surprising to see that storage of cleaned cartilage in the carbonated water retains its original shape and coloration for more than ten years, a much longer time than untreated cartilage sample, of example 1. This is also very much longer than might be anticipated by anyone skilled in the art of using $CO_2$ in extending the useful life of food substances.

Example 2a

This example illustrates the surprising difference between the product of our invention and the past art concerning the use of $CO_2$ in maintaining the usefulness of digestible substances. As shown in the following Table 2, the useful life of past art is measured in days while the product of our invention is shown useful after more than eight years.

TABLE 2

USE OF $CO_2$ IN MAINTAINING USEFULNESS OF DIGESTABLE SUBSTANCES

| | TIME | | | | | | | | | | |
|---|---|---|---|---|---|---|---|---|---|---|---|
| | 76 hours | 6 days | 16 days | 26 days | 3 mon | 6 mon | 12 mon | 2 years | 4 years | 6 years | 8 years |
| Our invention | useful | useful | useful | useful | useful | useful | useful | useful | useful | useful | useful |
| Coyne | useful | useful | useful | max useful | | | | | | | |
| Haines | max useful | | | | | | | | | | |
| Ogilvy | max useful | | | | | | | | | | |
| Anzuetto | useful | max useful | | | | | | | | | |

Coyne (Effect of Carbon Dioxide on Bacterial Growth with Special Reference to the Preservation of Fish"; J. Soc. Chem. Ind.; Vol 52; 1933; pp 19-24) studied the usefulness of 100% $CO_2$ compared to air in slowing the deterioration of a variety of fresh fish Haines (Influence of Carbon Dioxide on the Rate of Multiplication of Certain Bacteria as Judged by Viable Counts; J. Soc. Chem. Ind.; Vol 52; 1933; pp 13T-17T; 1933) studied the usefulness of 100% $CO_2$ compared to air in slowing the growth of *Pseudomonas, Proteus,* and *Achromobacter*, chief constituents of of the bacterial flora present on lean meat.

Ogilvy; (Post-Mortem Changes in Meats II. The Effects of Atmospheres Containing Carbon Dioxide in Prolonging the Storage Life of Cut-up Chicken; Food Technology; Vol 5, 1951; pp 97-102) studied the effect of 25% $CO_2$ on the prolonging the storage life of cut-up chicken Anzuetto; (Microatmospere Packaging of Apples; Inst. Of Food Tech. Annual Meet; Jun. 10-13, 1984) demonstrated the usefulness of 30% $CO_2$ on retarding decay of strawberries, only 8.3% decay after 6 days while untreated experienced 64.4% decay

Example 3

This example, among other things, demonstrates the surprising retention of effectiveness of cartilage stored by the technique of this invention in ameliorating the effect of arthritis. It also shows that some patients require a larger dose to see the advantages of our invention. A larger quantity of fresh sternum cartilage is obtained from a chicken processing facility and is prepared as in Example 2 and is cut into about one half gram pieces. About a one month supply of cartilage is then packaged, sealed and stored in each of many glass bottles each with the concentration of $CO_2$ as in Example 2. They are stored for over three years at room temperature. These samples are used to demonstrate that, after long term storage in $CO_2$ the cartilage retains its effectiveness.

After the storage period, the sample container is refrigerated then opened each day to remove a sample for consumption and quickly resealed to retain the $CO_2$. The cartilage is consumed by two females suffering from arthritis. The cartilage is consumed as relatively large pieces, often a single piece which is then chewed to reduce the particle size and allow it to be more easily adsorbed. One of the two female finds reductions in the symptoms of arthritis in about a week and the reduction continues to increase most significantly over the first month with slower improvement continuing thereafter for many months. The second female sees little change at the lower dose but then sees a similar improvement when the dose is five times the lower dose. This demonstrates that some patients require a higher dose to trigger the oral tolerization process. The cartilage containing type II Collagen, stored long term in aqueous $CO_2$, is surprisingly shown to have retained its effectiveness in ameliorating the effects of arthritis in humans.

Example 3a

This example, among other things, demonstrates that, effectiveness remains after being stored in aqueous $CO_2$, then removed from the water containing $CO_2$ and stored for short terms at low temperature. Example 3 is repeated except after opening a sealed glass bottle containing about one month supply of cartilage, the cartilage particles are drained and put into a plastic bag and are slowly frozen and stored. A therapeutic amount of this cartilage is consumed each day by two other females with beneficial results.

Example 3b

This example, among other things, demonstrates the effectiveness of the product of our invention in treating other species of warm blooded animals. Example 3 is repeated except dogs are used. The amount of cartilage in each bottle is reduced. This reduction is to supply about the same cartilage to weight ratio as in the human example. For dogs the stored cartilage is cut into small particles before consumption. A group of dogs suffering from osteoarthritis are given cartilage similarly to humans in Example 3 and similar beneficial results are seen.

Example 3b2

This example, among other things, further demonstrates that storage of undenatured cartilage containing type II collagen in the presence of aqueous $CO_2$ is capable of maintaining or improving the effectiveness of that stored cartilage in ameliorating the symptoms of arthritis over long periods of time. As in example 2, cartilage samples are stored for over three years in aqueous $CO_2$ at room temperature except the samples have had an additional 6 months of storage time in aqueous $CO_2$ as in example 3b. A group of dogs suffering from osteoarthritis are given cartilage and similar, but slightly superior beneficial results are seen. This example again indicates that long term storage in aqueous $CO_2$ maintains or even improves the effectiveness in ameliorating the effects of arthritis.

Example 3c

This example, among other things, demonstrates the surprising ability of the product of our invention to show a preventative effect when given to warm blooded mammals before the occurrence of autoimmune arthritis, such as osteoarthritis. The procedure of Example 3b is repeated except a group of older dogs is chosen from a breed that is particularly susceptible to osteoarthritis but have not yet contacted it. The dogs are dosed as above over a period of two years. The incidence of osteoarthritis in this dosed group is compared to a matched group of un-dosed dogs. The dosed dogs are found to have a very significant reduction in the incidence of osteoarthritis.

The result of this Example demonstrates a surprising, and previously unknown potential of the product of this invention to reduce the incidence of arthritis. This discovery has tremendous potential to reduce the incidence of arthritis in all warm blooded mammals. The use of undenatured chicken cartilage and many pharmaceuticals have shown an ability to reduce suffering from arthritis once it has begun its painful and devastating progress. However, the instant invention is the first to surprisingly show the ability to reduce the inception of arthritis. The product of our invention appears to serve as an apparent "vaccine" against osteoarthritis.

Example 3c2

This example further illustrates the improved effectiveness of the product of this invention compared to the product of the '820 patent in the treatment of dogs already afflicted with osteoarthritis. Twenty older dogs are selected that are already arthritic and overweight. These dogs are divided into two groups. The first group is randomly selected and treated once a day with the product of the '820 patent containing 10 mg of undenatured type II collagen as dried product. The second group is fed an equivalent amount of type II collagen that had been stored in small glass bottles for over one year in the presence of aqueous $CO_2$. In all cases they are fed close to or during meal time. Overall pain is measured on a scale of 1 to 10 with 1 being no visible pain and 10 being severe and constant pain. A physical examination is performed once a month. The dogs are examined rising from a sitting and laying down position as well as laying down from a standing position. The results shown in Table 3 further illustrates the superior performance of the product of this invention and the benefits of the storage of chicken cartilage in carbonated water.

TABLE 3

PERFORMANCE OF $CO_2$ STORED CHICKEN CARTILAGE BASED ON OVERALL PAIN LEVEL FOR ARTHRITIC DOGS

| | TIME | | | | |
|---|---|---|---|---|---|
| | 0 DAY | 30 DAY | 60 DAY | 90 DAY | 120 DAY |
| U.S. Pat. No. 7,083,820 Product | 4.8 | 3.2 | 2.6 | 2.3 | 1.8 |
| This Invention | 4.8 | 2.9 | 2.3 | 1.9 | 1.5 |

Example 3d

This example, among other things, demonstrates effectiveness of the product of our invention with horses. It also shows that after amelioration of the symptoms of arthritis that continued usage can surprisingly prevent reoccurrence. The procedure of Example 3 is repeated except a horse suffering from severe arthritis is dosed for several months with a similar cartilage to weight ratio, then varied to find a preferred dose. Significant improvement in the horse's symptoms is seen. When the administration of cartilage is stopped the symptoms return within days. When administration of the $CO_2$ stored cartilage is resumed the improvement resumes. In addition to demonstrating effectiveness with horses this example demonstrates the ability to prevent re-occurance. An additional advantage is seen in that wet product of the instant invention adheres to the dry grain and is nearly completely consumed. In contrast, the dry product of the '820 invention tends to separate from the grain settle to the bottom of the serving dish and be refused by the horses and more than 10% is thus wasted.

Example 3e

This example, among other things, demonstrates the superiority of the product of this invention over the dried product of the prior art. This example also demonstrates the surprising effect that some mammals require a larger dose to activate the desired oral tolerization effect. In order to demonstrate the superior performance of the $CO_2$ stored cartilage a comparative example to the prior art of Schilling's U.S. Pat. No. 7,083,820 a study is arranged. The procedure of Example 3b is repeated and a matched group of dogs is chosen that have arthritis. The product of '820 is purchased from Swanson under the trade name of UCH. The UCII capsule, according to the label contains 10 mg of undenatured type II collagen. When the matched group is dosed with an equivalent amount of the UCII, improvements in the arthritis symptoms in the dogs are seen. These improvements, however, are statistically seen to be significantly less than the improvements for the undenatured Type II collagen of the instant invention. Thus the superiority of the product of the instant invention is further demonstrated.

Example 4

This example, among other things, demonstrates the effectiveness of a uniform slurry of the product of this invention. A quantity of fresh sternum cartilage is obtained from a chicken processing facility. The cartilage is stripped of adhering flesh. The cartilage is then treated at room temperature in a dilute solution of NaOCl (about 1½%) for about 20 minutes. The cartilage is drained, rinsed with carbonated water and reduced in size with a slicing tool then placed into a container which contains 3% stabilized $H_2O_2$ in water. After about one hour, the fine sliced and then cross sliced cartilage is drained to remove excess hydrogen peroxide. Several bottles of club soda are purchased to store the sliced cartilage in an aqueous $CO_2$ environment. A small amount of the carbonated water is drained from each bottle and the drained cartilage is added to produce a slurry of about 10% cartilage. The capped, cartilage containing, bottles are stored at room temperature until shortly before use when they are refrigerated. Once a cooled container is opened, to begin using, it is then continuously maintained cool in order to slow $CO_2$ loss. Before each use the container is mildly agitated to produce a uniform slurry which is then poured to measure a uniform dose. This product is then shown to be effective in ameliorating the symptoms of arthritis.

Example 4a1

This example, among other things, demonstrates one of many alternate methods for the preparation of the product of our invention in aqueous slurry form. Example 4 is repeated except the slurry is prepared in a common 6 cup food "chopper/blender", model RIVAL model TB-170 sold by Wal-Mart. As in example 4, A quantity of fresh sternum cartilage is obtained from a chicken processing facility. The cartilage is stripped of adhering flesh. The cartilage is then treated at room temperature in a dilute solution of NaOCl (about 1½%) for about 20 minutes. The cartilage is drained, rinsed with carbonated water and placed into a container which contains 3% stabilized $H_2O_2$ in water. After about one hour the cartilage is drained to remove excess hydrogen peroxide. Forty three grams of clean cartilage are placed into the blender along with 391 grams of bottled soda water along with 6 ice cubes weighing about 17 g each. The blender is operated for 6 minutes then half of the resulting slurry is placed into ordinary kitchen carbonator and carbonated with a standard $CO_2$ capsule. The product is stored in a sealed bottle for about 6 months. This product is then shown to be effective in ameliorating the symptoms of arthritis.

Example 4a2

This example, among other things, demonstrates effective use of cartilage slurries at a higher solids level. Example 4a1 is repeated except at a higher solids level of 20% by weight. In this case the $CO_2$ content is increased by about twenty percent. The product is similarly effective. The upper limit of solids will be apparent to those familiar with the art of liquid/solid slurries and will be effected by the particle size and shape. Suspending agents such as methylcellulose and the like will also have an effect on both the achievable solid content and settling rate.

Example 4a3

This example, among other things, demonstrates that it is unnecessary to remove attached tissue when the product is in slurry form. Example 4a1 is repeated except with "as received cartilage" that is not stripped of the attached tissue. In this sample, which appears to be typical, it is found that the cartilage contains 16.4% by weight of attached material. Other than a slight increase in slurry viscosity no difference in appearance is seen between the produce of example 4a1 and this product. The product is stored in a sealed bottle for about 6 months. This product is then shown to be effective in ameliorating the symptoms of arthritis.

Example 4a3

This example, among other things, demonstrates the value of the use of antifoam additive in preparation of the product of this invention in slurry form. Example 4a1 is repeated except immediately prior to use of the blender a small amount of food grade silicon anti foam is added. This addition is found to improve the process by reducing the time required for the foam to dissipate both during the blending and carbonation steps. There are many other compounds that might be used to reduce foam which will be apparent to those skilled in the foam reduction art.

Example 4b

This example, among other things, demonstrates the beneficial effect of flavor enhancing and/or pH lowering additives. Example 4 is repeated except in addition to the $CO_2$, a small amount of phosphoric acid is added in an amount to reduce the pH to about 3.0. The product is found to be similarly effective and has an improved flavor.

Example 5

This example, among other things, demonstrates the ability to effective use a wide variety of water based liquids in the practice of the instant invention. It also demonstrates that larger doses are required for some consumers. Example 4 is repeated to prepare the fine sliced cartilage to the point that it is drained of excess hydrogen peroxide. In a manner similar to Example 4 the cartilage is placed into containers to produce a slurry with about 10% solids. The containers are then filled with a wide variety of liquids that would normally be considered to be safe and pleasant to consume by humans. Other containers are then filled with a variety of liquids that would normally be considered to be safe, promoting of improved health, and/or pleasant for canines, or equines to consume. The containers are then carbonated with $CO_2$, using a common kitchen type carbonator with a small cartridge containing $CO_2$, to about the same level as for club soda or more. Other pressurization techniques are well known in the carbonation of beverage art could be used with similar effect. After carbonation the bottles are stored at ambient temperature until opened after which refrigeration is preferred to help retain $CO_2$ for short term storage periods. As in example 4 the multiple products are shown to be effective in ameliorating the symptoms of arthritis.

It is found convenient to store multiple doses in a single bottle and to measure single doses from a gently agitated bottle. It is also found convenient to package a single dose per container, which can then be consumed completely. For some it is found useful to consume larger quantities or to consume the same quantity two or more times per day, or to, alternately, consume larger initial (sometimes called loading doses) doses then to gradually reduce dose size until a level is found that is not effective. The dose is then increased back to the lowest previously demonstrated effective dose.

Example 6

This example, among other things, demonstrates the superior performance of the product of this invention compared to the product of prior art. In this example cartilage that has been prepared according to U.S. Pat. No. 7,083,820, which is assumed to have been dried in the presence of potassium chloride, is purchased as UCII from Swanson. The fine ground cartilage is then soaked in club soda to remove the KCl and any other water soluble materials. The cartilage is then filtered, washed with club soda and re-suspended in club soda. The cartilage is found to be effective in ameliorating the symptoms of arthritis. This product, however, is slightly less effective than the product of the instant invention.

Example 7

This example, among other things, demonstrates the usefulness of alternatives to the salt of '820 to maintain the sterility during drying. This example produces a product that, is as effective or only slightly less effective than the major product of this invention. Example 4 is repeated except after treating with hydrogen peroxide, the cartilage is reduced in size and then dried at 110 F and then reduced in size in an impact type apparatus. Instead of using salts as in the '820 patent, a small amount of an antibacterial gas, chlorine in this case, is maintained in the recirculating air stream. In several steps, the amount of chlorine is increased until a level is found that prevents biological growth during drying in an equivalent manner to that of the salts of the '820 patent. In this case the warm air is cooled to condense and remove water then reheated before being returned to the drying chamber. A small make up supply of chlorine is added to replace that amount removed with the condensed water. The resulting dried, then fine ground product is suspended and stored in $CO_2$ containing water. After several months of storage the product is found to be as effective or nearly as effective in amelioration of the symptoms of arthritis as the non dried product and is found to produce a more uniform slurry and to settle more slowly.

Example 7a

This example, among other things, demonstrates other antibacterial gasses may be used in place of chlorine. Example 7 is repeated except chlorine is replaced with ethylene oxide as the antibacterial gas, with similar beneficial results. It is possible to operable with air as the drying medium and stay well below the explosive limit. To eliminate the possibility of accidentally exceeding the explosive limit, with tragic results, nitrogen is used with ethylene oxide in place of air for the first experiment. In a second experiment $CO_2$ replaces the nitrogen. As in example 7, the re-suspended, in aqueous $CO_2$ product, is found to be effective in ameliorating the symptoms of arthritis.

Example 7b

This example, among other things, demonstrates the usefulness of $CO_2$ as a gas during drying. Example 7 is repeated except drying takes place in a $CO_2$ atmosphere with an effective amount of chlorine gas added. A lower level of Cl2 is required than in example 7. As in Example 7 the product is found to be effective in ameliorating the effects of arthritis

Example 7c

This example, among other things, demonstrates the usefulness of ultraviolet light as an antibacterial agent during drying. Example 7b is repeated an effective amount of ultraviolet light is used as the antibacterial agent during drying.

Example 8

This example, among other things, demonstrates the ability to grind cartilage that has been slow frozen then ground at low temperature in the presence of dry ice or liquid nitrogen. Example 4 is repeated except the size reduction is carried out using slow frozen cartilage prepared as in example 15, in the presence of a small amount dry ice which is slowly added to an impact type apparatus. It is found that at the low temperature the cartilage is brittle enough to be easily ground. This procedure also allows temperature control which further allows more rapid grinding without over heating. When the preferred $CO_2$ is used, this procedure has the added advantage of intimately exposing the new cartilage surface to the beneficial effect of $CO_2$. When suspended in aqueous $CO_2$ the product is found to produce a more stable slurry due to the finer particle size. The product is stored for over one year then found effective in ameliorating the effect of arthritis.

Example 9

Example 8 is repeated except the dry ice is replaced with a cooling quantity of liquid nitrogen. In some cases it is found desirable to add $CO_2$ or chlorine or another antibacterial gas to gain the antibacterial benefits during grinding.

Example 10a1

This example, among other things, demonstrates the ability to utilize relatively thin flexible plastic containers with good gas barrier properties to store the product of this invention. Example 4a1 is repeated except the container is changed. Instead of storing in a large rigid container, the cartilage in aqueous $CO_2$ is stored in a flexible plastic "pouch". While any relatively non-permeable flexible plastic would do, we use a 4 mil vinyl chloride/vinylidene chloride copolymer, formerly sold under the trade name of SARAN. The container is filled in a $CO_2$ atmosphere then placed in a pressure chamber at about 20 psig of $CO_2$ pressure where it is heat sealed. The product is stored for over one year at room temperature then found effective in ameliorating the effect of arthritis. Part of that time the container was stored in a vessel pressurized with about 5 psig of $CO_2$.

Example 10a2

This example, among other things, demonstrates the usefulness of higher permeable flexible packages when stored in a $CO_2$ atmosphere. Example 10 is repeated except a more permeable plastic is used for the individual packages. In this case a lightly plasticized Polyvinyl chloride film is used. After filling the capsules are placed in a metal pressure vessel which is then filled with 20 psig of $CO_2$ for long term storage. It is found that after removal from the 20 psig atmosphere the individual packets retain their usefulness for many days at room temperature. This useful time is extended when the external $CO_2$ pressure is reduced by storing product under refrigeration. This process is most useful in cases requiring a large number of doses to be administered in a short period of time. This example uses a facility housing many equine mammals, horses in this case. Plastic vessels, particularly plasma coated, and other vessel types known in the art may be substituted for the metal pressure vessel.

Example 10b

This example, among other things, demonstrates ability to produce small single dose packages using the product of the instant invention. The technique of Example 10a1 is used to produce small single dose packages. These packages are stored for over one year then found effective in ameliorating the effect of arthritis. For part of this time the packages are stored in a pressure vessel with a $CO_2$ atmosphere.

Example 10c

This example, among other things, demonstrates the ability to produce many single dose packages on a single sheet. The technique of Example 10b is used to produce single dose packages with multiple doses on a single sheet. In the pharmaceutical area these are often called "bubble packs". In this case the single doses are separated by perforations that allow easy tearing for removal of a single dose or multiple single doses. It is desirable to have each removable segment imprinted with pertinent information such as the cartilage name, dose, time, and date.

Example 11

This example, among other things, demonstrates the ability to vacuum dry cartilage then grind. The cartilage is first slowly frozen, as in example 15. Example 4 is repeated except after treating with hydrogen peroxide, the cartilage is slowly frozen then vacuum freeze dried at a temperature slightly below 32 F until the moisture content is low enough to allow grinding ease. The freeze dried product is found to have a porous structure which surprisingly renders it much easier to grind. Depending on the grinding process there is an optimum level of moisture. In this case the moisture is below about 5%. The product is then ground and utilized as in Example 7. When the moisture content is varied upward and low temperature grinding used, it is found possible to produce a finely ground product that has no detectable loss in undenatured type II Collagen over a range of moisture contents. Depending on the comminution process selected an optimum level will be found by those familiar with the grinding art. A higher moisture content is generally preferred where possible since it is more readily absorbed.

Example 12

This example, among other things, demonstrates the ability of water soluble thickening type agents to slow the separation of cartilage solids and, when added at lower levels, to stabilize suspensions. Example 4 is repeated except a water soluble thickening agent is added to the blend of $CO_2$ containing water and the cartilage. There are a wide variety of such useful thickening agents known to those skilled in the art. In this case methyl cellulose is used to provide a medium viscosity slurry. The suspension is seen to retain its uniformity over a wider period of time without the need to agitate as frequently, or to agitate at all. The thickened aqueous solution containing the cartilage and $CO_2$ is shown to retain its effectiveness in ameliorating the effects of arthritis in humans. When added at lower levels, the methyl cellulose thickening agent is seen to improve the stability of the suspension with only a neglectable or very small increase in viscosity. This suggests surface activity to cause particles in some way to repeal each other.

Example 12a

This example, among other things, demonstrates the ability to add water soluble polymers at higher levels to form non separating "slurries". It is found that it is possible to thicken the material to about the consistency of tooth paste and package into single dose pouches as in Example 10 b. These pouches are found to be particularly desirable and effective in dosing horses as in Example 3d. It is further found possible to place the tooth paste consistency material into tooth paste type containers and then to expel a dose at a time, then recap as in tooth taste use. As shown in previous examples various materials and storage conditions are useful.

Example 13

This example, among other things, demonstrates the use of a technique for dose metering from a larger reservoir of the product of our invention. There are many ways to meter a dose known to those familiar with metering techniques and devices. A particularly desirable technique is to use overflow devices on a volumetric unit that is built into a container for a large number of doses. Such a device is fabricated using polyethylene terephthalate. Cartilage prepared as in Example four is stored for several months in this container in the presence of $CO_2$. The bottle is very gently agitated to promote uniformity before each use, then the sides are compressed to force a dose into the metering chamber when the compression is released the excess fluid overflows the metering chamber and returns to the reservoir in the body of the bottle. The bottle is refrigerated before the initial opening and the bottle is then stored under refrigeration both to conserve the $CO_2$ atmosphere, and to prevent expulsion of fluid from the bottom reaching metering tube. After consuming for about a month, an elderly man is found to have greatly reduced symptoms of osteoarthritis demonstrating the effectiveness of the undenatured cartilage stored and dispensed in this manner. As in earlier examples, escape of carbon dioxide can be prevented by storing the entire containers under a few psig of carbon dioxide.

Example 14

This example, among other things, demonstrates the surprising effect of storage temperature on useful storage life of the product of the instant invention. A series of slurry samples are prepared using the procedure of example 4a1. These samples are stored at a variety of temperatures for 12 months then tested for effectiveness. It is surprising to note that lower storage temperatures are not as useful as ambient temperatures in maintaining effectiveness for ameliorating the effect of arthritis. It is found that a temperatures of 60 to 90 degrees F. are most effective while temperatures of 55 to 95 are useful. Temperatures as low as about 35 degrees or above about 100 degrees are found to be undesirable while temperatures of 35 to about 55 degrees show less effectiveness. Normally lower storage temperatures would be expected to increase the retention of effectiveness of the undenatured cartilage. This surprising, and unexpected effect of reduced effectiveness of material stored at lower temperature is completely unexpected. This unexpected behavior is not understood but perhaps it relates to the reduced partial pressure of the $CO_2$ at the lower temperatures. The reduction of effectiveness above about 100 degrees is in line with expectations and these experiments simply help to define the limits of our invention.

Example 15

This example demonstrates that rapid freezing of untreated cartilage denatures a significant portion of the cartilage while slow freezing does not. As in example 3, a quantity of fresh sternum cartilage is obtained from a chicken processing facility. A sample is flash frozen in minutes with extremely low temperature air using a technique that is common to processing chicken. Another sample is slow frozen over a period of several days by placing it into a thick wall, foamed polystyrene container which is then placed into a freezer where the temperature is minus 10 degrees F. The fast frozen sample and the slow frozen sample are both subjected to a measure of the amount of undenatured cartilage remaining using the Enzyme-linked immunosorbent assay (ELISA) technique with a special adaptation that has been developed to detect undenatured type II collagen. Surprisingly the fast frozen sample shows significant loss of the undenatured cartilage while the slow frozen sample shows no significant reduction in undenatured cartilage. This totally unanticipated result allows freezing of the raw cartilage to be used to prepare the product of our invention. The cartilage can then be stored in larger batches with obvious processing advantages. These advantages become even more apparent as consumer demand for this product increases to require large scale manufacturing. One advantage is the ability to use freeze drying under a vacuum or low temperature grinding, where the cartilage becomes brittle. When an additional sample of cartilage is frozen over a period of several hours undenatured cartilage is again shown to be essentially unchanged. Further simple variations will define the shortest freezing times that do not cause cartilage to be denatured. These times will vary with the conditions such as temperature, size of the freezing batch, other heat transfer conditions, or for a continuous process. Persons or engineers familiar with the art of heat transfer will readily determine optimum conditions for a particular application. Perhaps the rapid expansion of water associated with rapid freezing breaks essential molecular bonds while slower freezing allows time for molecular structures to relax and reorient to avoid the breaks.

Example 16

This example, among other things, demonstrates the use of type II collagen contained in the vitreous humor of eyes to both ameliorate the effect of arthritis and to produce nearly transparent suspensions.
Fresh porcine eyes were acquired from a pig slaughter house. These eyes were less then 36 hours post mortem and had been stored at 5 C.° in a saline solutions. They were obtained from 3-6 month old Chester Whites weighing from 50 to 100 kg. Vitreous humor was removed from the eye. After carefully removing a highly pigmented ring the remaining vitreous humor is placed into a blender with aqueous $CO_2$ where they are blended for 6 minutes then additional $CO_2$ added in the previously defined Kitchen carbonator. The product is found to have a degree of transparency. Transparency is a very desirable feature for market appeal. After several months storage, aqueous $CO_2$ product is used to treat arthritic dogs. After trials to determine an effective amount of the slurry, the product is found effective in ameliorating the effects of arthritis in these cannines.

Example 17

This example demonstrates a difference in the vitreous humor quality and quantity, depending on the mammal species.
Porcine eyes of example 16 are compared to bovine eyes.

|  | Initial solids wt % | non soluble solids wt % | vitrious humor | eye weight |
| --- | --- | --- | --- | --- |
| Porcein Eyes | 0.32 | — | 2.6 g | 6.8 g |
| Bovine Eyes | 1.3-1.7% | 0.95% | 14.7 g | 26 g |

It is seen that porcine eyes are smaller and thus have much less vitreous humor than the cattle eyes. It is likewise seen that the solids content is much lower. Since it is the solids that contain the type II collagen, it is seen that the quality is higher in the bovine eyes. Bovine eyes are preferred for the practice of our invention.

Example 18

This example demonstrates the relative ease of reducing the particle size of the collagen contained in vitreous humor (VH). This is accomplished by first placing the vitrious humor from several cow eyes into the blender used in example 4a1. Chopping the VH, along with carbonated water, and Ice cubes in the blender, produces a uniform slurry of medium sized particles of VH which is then passed through a small diameter tube under high pressure which further reduces the particle size. By passing the slurry through successively smaller tubes under higher and higher pressure an extremely fine dispersion is produced. When a small amount of water soluble polymer is added, methyl cellulose in this case, stability of the suspension is increased. When the initial VH is dispersed in water it apparently matches the refractive index of the water and is invisible. When placed into carbonated water, however, the collagen II containing tissue slowly separates and becomes visible. Thus it is important to do the size reduction rapidly once introduced into the carbonated water.

Example 19

This example demonstrates a technique for removing the "strongly pigmented circle" from the vitreous humor. This is removed by hand only with great difficulty and with a significant loss of vitreous humor when done at ambient temperature. This is because of the elusive nature of the "circle" that makes it difficult to capture and remove. This nature also makes it more difficult to maintain microbe free conditions.

It is found that the pigment removal operation is easy to perform on either frozen eyeballs or on the removed and frozen vitreous humor. Five cow eyeballs are frozen slowly so as to not denature the collagen. They are then dissected free of surrounding tissue while still frozen. When this tissue is removed the pigment circle is visible and more easily removed.

The cleaned vitreous humor is stored frozen until further processing is desired, then it is thawed and processed as in example 18. It is found desirable, during thawing, to expose the vitreous humor to NaOCl and $H_2O_2$ in the manner of Example 2 to improve sterility.

Example 20

This example, among other things demonstrates the surprising; ability of the product of our invention to show a preventative effect when given to warm blooded mammals before the occurrence of osteoarthritis. Following the procedure of Example 3c a group of 6 older, same age, horses that have not yet contacted osteoarthritis are divided into two groups of three each. Three of the horses are given a daily, weight adjusted dose while the other three are treated the same in every way but are not given the preserved chicken cartilage. Over a period of years it is seen that all of the untreated horses develop symptoms of osteoarthritis much sooner than the horses treated with the product of our invention. This discovery will be of particular importance in adding years of peak performance to competitive horses. It is also important to add years of pain free life and usefulness to common horses and those classified as pets.

Example 21

This example, among other things demonstrates the surprising; ability of the product of our invention to show a preventative effect when given to warm blooded mammals before the occurrence of osteoarthritis. Following the procedure of Example 3c a group of 12 older, same age, people who have not yet contacted osteoarthritis are divided into two groups of 6 each. Each group contains 3 males and 3 females. The first group receives no treatment while the second group of 6 receives a dose of the undenatured product of this invention. It is found that the product of our invention is successful in either preventing, reducing the effect, or delaying the symptoms of osteoarthritis when compared to the control group.

CONCLUSION

While the instant invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains.

What is claimed is:

1. A method for the reduction of the occurrence of the symptoms of osteoarthritis in a horse comprising the steps of: (a) separating chicken cartilage containing water-insoluble undenatured Type II collagen from chicken tissue to produce separated chicken cartilage; (b) sterilizing said separated chicken cartilage under conditions which do not change the original structure of the Type II collagen to produce a prepared chicken cartilage; (c) storing said prepared chicken cartilage for more than six days but less than eight years at room temperature in an aqueous medium comprising more than 0.3 percent carbon dioxide by weight without microbial spoilage of the prepared chicken cartilage; and (d) orally administering a quantity of said stored chicken cartilage containing at least about 0.01 grams of Type II collagen on a daily basis to the horse to reduce the occurrence of the symptoms of osteoarthritis in the horse.

2. The method of claim 1, wherein in step (b) the separated chicken cartilage is sterilized with an antimicrobial agent selected from the group consisting of sulfur dioxide, ethylene oxide, chlorine, sodium hypochlorite and hydrogen peroxide.

3. The method of claim 1, wherein in step (b) the separated chicken cartilage is sterilized by exposure to radiation selected from the group consisting of x-rays, gamma rays, electron beams and ultraviolet light.

4. The method of claim 1, wherein in step (b) the separated chicken cartilage is first washed with an aqueous solution comprising sodium hypochlorite and then washed with an aqueous solution comprising hydrogen peroxide and finally rinsed with water.

5. A method for the reduction of the occurrence of the symptoms of osteoarthritis in a human comprising the steps of: (a) separating chicken cartilage containing water-insoluble undenatured Type II collagen from chicken tissue to produce separated chicken cartilage; (b) sterilizing said separated chicken cartilage under conditions which do not change the original structure of the Type II collagen to produce a prepared chicken cartilage; (c) storing said prepared chicken cartilage for more than six days but less than eight years at room temperature in an aqueous medium comprising more than 0.3 percent carbon dioxide by weight without microbial spoilage of the prepared chicken cartilage; and (d) orally administering a quantity of said stored chicken cartilage containing at least about 0.01 grams of Type II collagen on a daily basis to the human to reduce the occurrence of the symptoms of osteoarthritis in the human.

6. The method of claim 5, wherein in step (b) the separated chicken cartilage is sterilized with an antimicrobial agent selected from the group consisting of sulfur dioxide, ethylene oxide, chlorine, sodium hypochlorite and hydrogen peroxide.

7. The method of claim 5, wherein in step (b) the separated chicken cartilage is sterilized by exposure to radiation selected from the group consisting of x-rays, gamma rays, electron beams and ultraviolet light.

8. The method of claim 5, wherein in step (b) the separated chicken cartilage is first washed with an aqueous solution comprising sodium hypochlorite and then washed with an aqueous solution comprising hydrogen peroxide and finally rinsed with water.

\* \* \* \* \*